US011013631B2

(12) United States Patent
Jenkins, III

(10) Patent No.: US 11,013,631 B2
(45) Date of Patent: May 25, 2021

(54) DYNAMICALLY REACTIVE SPINAL SUPPORT SYSTEM

(71) Applicant: Arthur L. Jenkins, III, Greenwich, CT (US)

(72) Inventor: Arthur L. Jenkins, III, Greenwich, CT (US)

(*) Notice: Subject to any disclaimer, the term of this patent is extended or adjusted under 35 U.S.C. 154(b) by 0 days.

(21) Appl. No.: 14/180,517

(22) Filed: Feb. 14, 2014

(65) Prior Publication Data

US 2014/0296653 A1     Oct. 2, 2014

Related U.S. Application Data

(60) Division of application No. 13/195,826, filed on Aug. 1, 2011, now Pat. No. 8,708,940, which is a
(Continued)

(51) Int. Cl.
*A61F 5/01*     (2006.01)
*A61B 5/11*     (2006.01)
(Continued)

(52) U.S. Cl.
CPC ........ *A61F 5/0102* (2013.01); *A41D 13/0531* (2013.01); *A61B 5/02042* (2013.01);
(Continued)

(58) Field of Classification Search
CPC ........ A61L 15/12; A61L 15/125; A61L 15/07; A61L 15/14; A61L 15/08; A61L 15/58; C08L 75/04; C08L 33/24; C08L 29/04; C08L 83/04; A61F 13/04; A61F 15/001; A61F 5/01; A61F 5/05825; A61F 5/0585; A61F 13/041; A61F 5/058; A61F 13/02; A61F 13/107; A61F 15/00; A61F 15/02; A61F 5/055; A61F 5/05; A61F 5/05841;
(Continued)

(56) References Cited

U.S. PATENT DOCUMENTS 3,680,548 A * 8/1972 Brown .............................. 602/7
4,589,407 A     5/1986 Koledin et al.
(Continued)

*Primary Examiner* — Keri J Nelson
(74) *Attorney, Agent, or Firm* — Welsh IP Law LLC

(57) ABSTRACT

A brace device for the support of a wearer. The brace device comprises a flexible smart fabric, operable to partially or substantially enclose and/or lie adjacent to one or more portions of the thoracic, lumbar and/or cervical portions of the spine of the wearer. Fabric hardening means are provided, operable to partially or substantially harden one or more regions of the smart fabric upon application of an activating stimulus, thereby to prohibit, restrict and/or resist movement of one or more portions of the spine of the wearer. One or more predetermined regions of the smart fabric are in a substantially flexible configuration when the fabric hardening means are not activated, facilitating positioning, fitment and/or adjustment of the device around the wearer. Upon activation of the fabric hardening means, the one or more predetermined regions are operable to cause the one or more predetermined regions to assume a substantially rigid configuration and thereby partially or substantially support and/or immobilize of at least a portion of the spine of the wearer.

17 Claims, 6 Drawing Sheets

Related U.S. Application Data continuation-in-part of application No. 13/147,231, filed as application No. PCT/US2010/055043 on Nov. 2, 2010, now Pat. No. 8,551,030.

(60) Provisional application No. 61/257,793, filed on Nov. 3, 2009.

(51) Int. Cl.

| | | |
|---|---|---|
| *A61F 5/02* | (2006.01) | |
| *A41D 13/05* | (2006.01) | |
| *A61B 5/00* | (2006.01) | |
| *A61F 5/32* | (2006.01) | |
| *A61F 5/30* | (2006.01) | |
| *A61B 5/02* | (2006.01) | |
| *A61B 5/0205* | (2006.01) | |

(52) U.S. Cl.
CPC ............ *A61B 5/02055* (2013.01); *A61B 5/11* (2013.01); *A61B 5/6803* (2013.01); *A61B 5/6812* (2013.01); *A61B 5/6822* (2013.01); *A61B 5/6823* (2013.01); *A61F 5/02* (2013.01); *A61F 5/028* (2013.01); *A61F 5/30* (2013.01); *A61F 5/32* (2013.01); *A61B 5/6804* (2013.01); *A61B 5/6805* (2013.01); *A61B 5/702* (2013.01); *A61B 2562/028* (2013.01); *A61B 2562/0219* (2013.01)

(58) Field of Classification Search
CPC .... A61F 13/046; A61F 5/0111; A61F 5/0118; A61F 13/10; A61F 13/531; A61F 13/8405; A61F 15/004; A61F 5/02; A61F 5/028; A61F 5/30; A61F 5/32; A61B 5/6804; A61B 5/6812; A61B 5/6822; A61B 5/6823
USPC ...................................... 602/4–9, 16, 18, 19
See application file for complete search history.

(56) References Cited

U.S. PATENT DOCUMENTS

| | | | | |
|---|---|---|---|---|
| 4,594,999 | A | | 6/1986 | Nesbitt |
| 5,016,622 | A | * | 5/1991 | Norvell ............................ 602/7 |
| 5,437,614 | A | * | 8/1995 | Grim ............................... 602/19 |
| 5,626,151 | A | | 5/1997 | Linden |
| 6,036,664 | A | | 3/2000 | Martin et al. |
| 6,927,316 | B1 | * | 8/2005 | Faries et al. .................... 602/43 |
| 7,210,240 | B2 | * | 5/2007 | Townsend ............. A61B 5/1116 33/341 |
| 2002/0113417 | A1 | | 8/2002 | Mattes et al. |
| 2003/0212355 | A1 | * | 11/2003 | Shilling .................. A61F 5/026 602/19 |
| 2004/0183283 | A1 | * | 9/2004 | Buckman et al. ......... 280/730.1 |
| 2009/0024062 | A1 | * | 1/2009 | Einarsson ............ A61B 5/4528 600/595 |

* cited by examiner

DYNAMICALLY REACTIVE SPINAL SUPPORT SYSTEM

CROSS-REFERENCE TO RELATED APPLICATIONS

This application is a divisional application of U.S. patent application Ser. No. 13/195,826, filed Aug. 1, 2011, which itself is a continuation in part of co-pending U.S. patent application Ser. No. 13/147,231, entitled "Dynamically Reactive Spinal Support System", filed on Aug. 1, 2011 as a National Stage application of PCT/US2010/055043; claiming priority from U.S. Provisional Patent Application Ser. No. 61/257,793 filed on Nov. 3, 2009, the disclosures of which are incorporated herein by reference.

BACKGROUND OF THE INVENTION

This invention relates to a brace device; typically for the provision of dynamic support to the back and/or neck of a wearer engaged in high-risk activities, or for dynamic immobilization and support of a patient suffering from a spinal injury. The brace device has ready applicability in protective or preventative applications, including incorporation in helmets and padding used by racing car drivers, football players, and military personnel; and in medical applications, including cervical collars and other spinal bracing for trauma victims after an accident or injury.

The invention addresses the need to minimize abnormal movement of the head, neck, back and/or spine during an impact or collision, or other injury-causing sudden change in movement; providing rigidity that restricts the potentially injury-causing movements from being subjected to the spine, whether from the original impact or change in movement and/or upon subsequent recoil.

SUMMARY OF THE INVENTION

According to a first aspect of the invention there is provided a brace device for the spinal support of a wearer, the brace device comprising:
   a plurality of component parts, each component part being moveable relative to at least one other component part;
   movement sensing means, for monitoring the movement of at least one component part relative to at least one other component part with which it is moveable, the movement sensing means generating one or more output signals indicative of said movement or in response to a change in movement;
   movement resisting means, provided on one or more of said component parts and operable to prohibit, restrict and/or resist movement of at least one component part relative to at least one other component part; and
   control means in communication with the movement sensing means and the movement resisting means, the control means being programmed to interpret and/or analyze the said one or more output signals generated by said movement sensing means within predetermined parameters and/or criteria;
wherein one or more of the movement resisting means are dynamically controlled in response to one or more signals being received from the control means when the control means determines a movement or change in movement requires support of the spine of the wearer.

Typically the brace device is utilized in the mitigation or prevention of injuries to a wearer participating in high risk activities. Such activities typically involve a risk of significant impact to the body, back or head of the wearer, or to the vehicle or equipment with which the wearer may be associated.

Preferably, the brace device is arranged to have one or more component parts, alone or in combination with other component parts, substantially or partially encircle and/or lie adjacent one or more portions of the spine of the wearer; typically the neck, and more particularly, around the cervical and thoracic portion of the spinal column of the wearer. The component parts are typically plates. Preferably, the brace device is comprised of combined neck and chest collar portions.

Preferably, the movement sensing means and the movement resisting means are adapted to sense and resist linear, shear and rotational movement.

The movement sensing means may include one or more micro electro-mechanical accelerometers, gyroscopes, force-transducers, pressure sensors and/or strain gauges.

Preferably, the movement sensing means are adapted to sense the rate of change in velocity (acceleration/deceleration) and/or a change in inclination (pitch and/or yaw). The movement sensing means typically include an accelerometer and/or gyroscope, capable of detecting movement changes in three dimensions (triple-axis). Preferably, the movement sensing devices are micro electro-mechanical systems.

The movement sensing means may include the airbag deployment system and/or the dynamic stability control system of the vehicle in which the wearer is travelling.

Typically, the control means is an electronic microprocessor, connected by wire or connected wirelessly to the movement sensing means and the movement resisting means. Typically, the connections are flexible electrical conducting wires.

Typically, the component parts are operable to articulate, relative to one another, at one or more interfaces defined by the movement resisting means, whereby a tendency for a motion of one component part relative to another component part is prohibited, restricted and/or resisted. Alternatively, in certain situations, for example after an impact is subjected on a wearer, a tendency for the interface to remain in a statically abnormal immobilization configuration, or to urge further secondary movement between the component parts into a secondary configuration, may be permanently or temporarily assisted in order to prevent or mitigate further injury from rebound or recoil movement of the head and/or body of the wearer after an impact or other injurious event.

Typically, the component parts are adapted from moveable overlapping plates, preferably manufactured from a breathable fabric (for comfort), that is adapted to allow relatively free movement of the neck and head under normal circumstances, but provides immediate immobilization at the initiation of abnormal head, neck or spinal movement. The movement resisting means are typically located in the region of possible overlap.

Typically, the brace device may comprise means for generating a wireless distress signal, operable to notify emergency crews after the activation of the device.

One or more component parts may be tethered or otherwise connected to a helmet worn by the wearer. The helmet may itself be formed of one or more parts, at least one of which may act as a component part relative to the component parts of the brace device.

According to a second aspect of the invention there is provided a brace device for the spinal support of a wearer, the brace device comprising:

a flexible smart fabric, operable to partially or substantially enclose and/or lie adjacent to one or more portions of the spine of the wearer;

movement sensing means, for monitoring the movement of at least one location on the smart fabric relative to one or more other locations on the smart fabric and/or other portions of the brace device, the movement sensing means generating one or more output signals indicative of said movement or in response to a change in movement;

fabric hardening means, operable to partially or substantially harden one or more regions of the smart fabric upon application of a stimulus, thereby to prohibit, restrict and/or resist movement of one or more portions of the spine of the wearer; and control means in communication with the movement sensing means and the hardening means, the control means being programmed to interpret and/or analyze the said one or more output signals generated by said movement sensing means within predetermined parameters and/or criteria;

wherein one or more regions of the flexible fabric is dynamically controlled in response to one or more signals being received from the control means when the control means determines a movement or change in movement requires support of the spine of the wearer.

The smart fabric may be tethered or otherwise connected to a helmet worn by the wearer. The helmet may itself incorporate a smart fabric which may respond independently or in response to one or more signals being received from the control means.

According to another aspect of the invention, there is provided a brace device for the support of a wearer, the brace device comprising:

a flexible smart fabric, operable to partially or substantially enclose and/or lie adjacent to one or more portions of the muscular-skeletal system of the wearer;

movement sensing means, for monitoring the movement of the wearer and/or one location on the smart fabric relative to one or more other locations on the smart fabric and/or other portions of the brace device, the movement sensing means generating one or more output signals indicative of said movement or in response to a change in movement;

fabric hardening means, operable to partially or substantially harden one or more regions of the smart fabric upon application of a stimulus, thereby to prohibit, restrict and/or resist movement of one or more portions of the muscular-skeletal system of the wearer; and control means in communication with the movement sensing means and the hardening means, the control means being programmed to interpret and/or analyze the said one or more output signals generated by said movement sensing means within predetermined parameters and/or criteria;

wherein one or more regions of the flexible fabric is activated, deactivated or dynamically controlled in response to one or more signals being received from the control means when the control means determines a movement or change in movement requires support of the muscular-skeletal system of the wearer.

Preferably, the brace device of either aspect of the invention includes additional sensors for monitoring the physical condition or the wearer, including the heart rate, body temperature, blood pressure and the presence and/or location of bleeding.

According to another aspect of the invention, there is provided a brace device for the spinal support of a wearer, the brace device comprising:

a plurality of component parts operable in combination to be placed over substantially the thoracic, lumbar and/or cervical portions of the spine of the wearer, each component part being moveable relative to at least one other component part; and movement resisting means, provided on one or more of said component parts and operable upon activation to prohibit, restrict and/or resist movement of at least one component part relative to at least one other component part;

wherein one or more predetermined regions of the combination of component parts are in a substantially flexible configuration when the movement resisting means are not activated, facilitating positioning, fitment and/or adjustment of the brace device around the wearer, and upon activation of the movement resisting means are operable to cause the one or more predetermined regions to assume a substantially rigid configuration and thereby partially or substantially support and/or immobilize of at least a portion of the spine of the wearer.

Preferably, one or more of the component parts are shaped and/or contoured to correspond with a body habitus of an average wearer.

The movement resisting means may be electromagnetic locks that are operable to provide pre-tensioning around the wearer prior to locking.

A rod, having engaging means to engage the brace device, may be used to facilitate positioning of the brace device behind the wearer.

Preferably, one or more of the component parts are radiolucent and one or more radio-opaque component parts and/or movement resistant means are positioned to minimize potential overlap with the spinal anatomy of the wearer.

According to another aspect of the invention there is provided a brace device for the support of a wearer, the brace device comprising:

a flexible smart fabric, operable to partially or substantially enclose and/or lie adjacent to one or more portions of the thoracic, lumbar and/or cervical portions of the spine of the wearer;

fabric hardening means, operable to partially or substantially harden one or more regions of the smart fabric upon application of an activating stimulus, thereby to prohibit, restrict and/or resist movement of one or more portions of the spine of the wearer; and wherein one or more predetermined regions of the smart fabric are in a substantially flexible configuration when the fabric hardening means are not activated, facilitating positioning, fitment and/or adjustment of the device around the wearer, and upon activation of the fabric hardening means are operable to cause the one or more predetermined regions to assume a substantially rigid configuration and thereby partially or substantially support and/or immobilize of at least a portion of the spine of the wearer.

The hardening means and/or the applied stimulus may be thermal, chemical, mechanical, electrical or magnetic.

One or more predetermined regions of the brace devices may selectively be activated or deactivated.

The illustrations are intended to provide a general understanding of the concepts described and the structure of various embodiments, and they are not intended to serve as a complete description of all the elements and features of methods and systems that might make use of the structures or concepts described herein. Many other embodiments will be apparent to those of skill in the art upon reviewing the description. Other embodiments may be utilized and derived, therefrom, such that structural and logical substitutions and changes may be made without departing from the scope of this disclosure. It should also be appreciated that the figures are merely representational, and are not be drawn to scale and certain proportions thereof may be exaggerated, while others may be minimized. Accordingly, the specification and drawings, together with any examples, are to be regarded in an illustrative rather than a restrictive sense and the specific form and arrangement of the features shown and described are not to be understood or interpreted as limiting on the invention.

DESCRIPTION OF EMBODIMENTS

Figure 1:
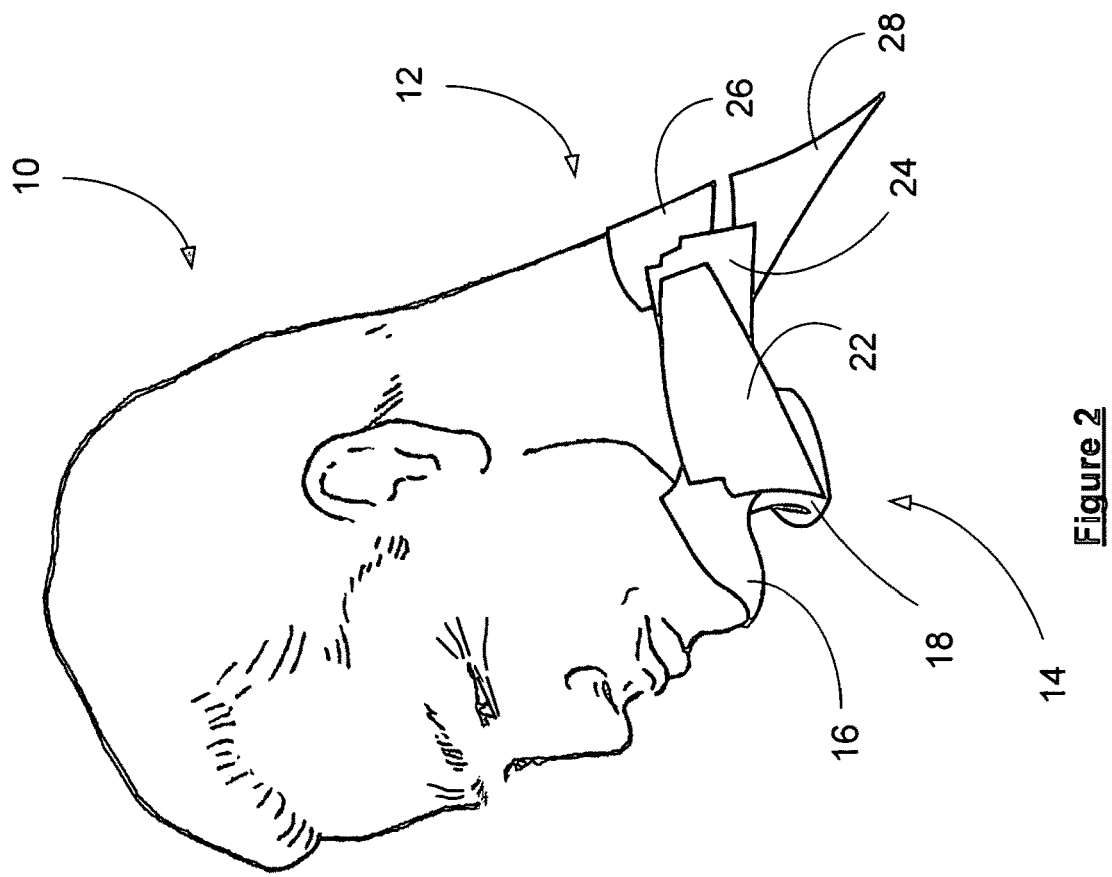
FIG. 1 shows the head and neck of a wearer fitted with a cervical collar brace device according to a first embodiment of the present invention, in a normal, free movement position.

In FIG. 1, a wearer's head 10 is depicted, with a simple electromagnetically activated cervical collar brace device 12 located around his neck 14.

The cervical collar 12 encircles the neck 14 of the wearer and is comprised of several moveable and overlapping component parts; including a central anterior superior part 16, a central anterior inferior part 18, a central anterior middle part 20, a left anterior lateral (visible) and a right anterior lateral part 22, a left posterior inferior (visible) and a right posterior inferior part 24, a central posterior inferior part 26 and a central posterior superior part 28.

It should be apparent, in the embodiment depicted in FIG. 1, that certain component parts are moveable relative to one or more other component parts in rotational, shear and/or linear orientations. For example, the interface between the left anterior lateral part 22 and the left posterior inferior) part 24 is rotatable and the combination of the two pieces may be extended or contracted. Together, the numerous component parts of the cervical collar brace device 12 allow relatively free movement of the head and neck under normal circumstances. However, immediate immobilization is initiated in the event of an abnormal neck movement being detected. All of the pieces are linked together, and the tethers that connect them will prevent the pieces from being unable to function when needed to limit movement.

Although a limited number of component parts are illustrated in FIG. 1, it should be readily apparent that the invention contemplates that more or less component parts could be incorporated in the brace device 12; more parts increasing complexity, but also affording increased flexibility of movement. The number, shape and size of the parts may be varied to accommodate differences in the size, shape, and purpose of the brace device. The component parts typically overlap over articulated interfaces; similar to the manner fish scales and ancient armor plating enable movement.

Figure 2:
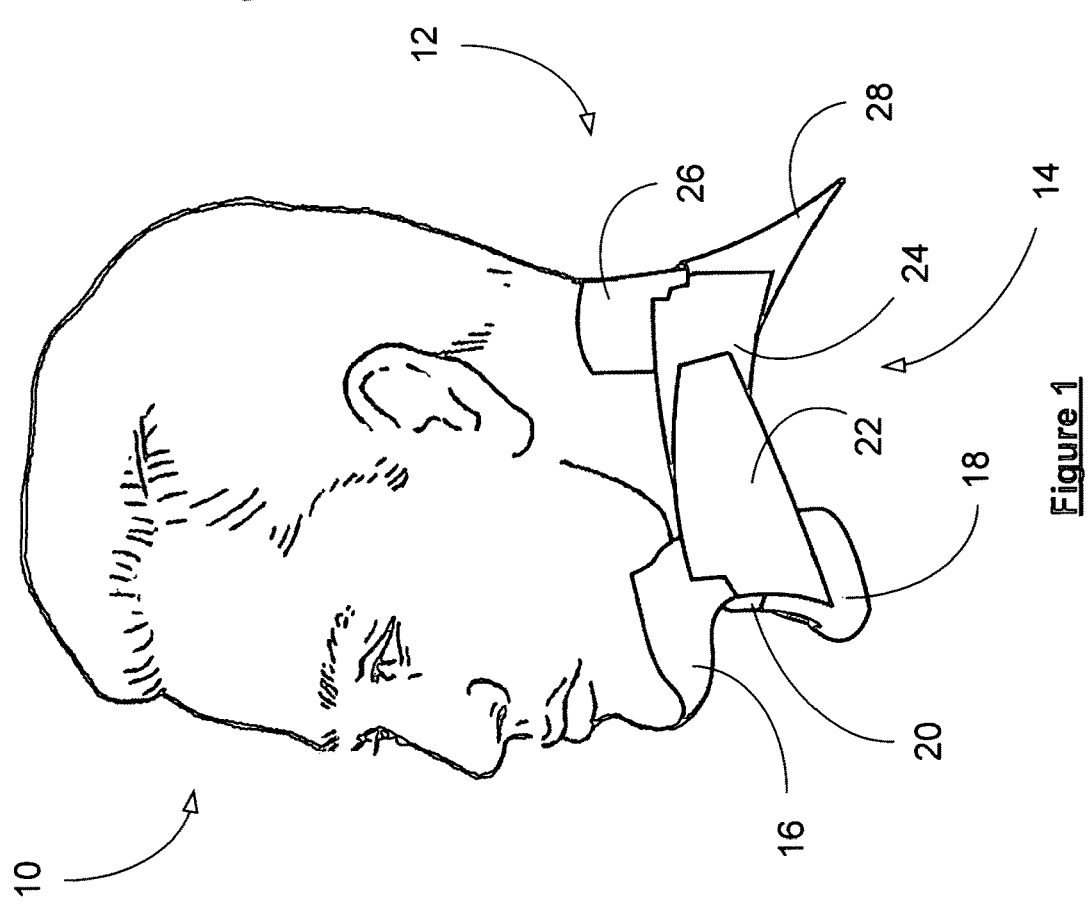
FIG. 2 shows the wearer and collar of FIG. 1, wherein the head and neck have been extended forward to a potentially abnormal position following an impact being subjected to the wearer, and the collar brace device has been engaged to restrict movement of the head and neck.

In FIG. 2, the wearer's head 10 has been subjected to an impact force directed substantially from in front of his original position. The wearer may have been moving forward and then stopped suddenly (such as in a collision), or he may have been pushed backwards suddenly (such as in a tackle in football). In either event, the resultant movement causes an improper and abnormal extension of the neck at the rear, and an accompanying compression of the vertebrae at the front, as the head is propelled forward.

The impact has subjected considerable force on the wearer 10 and this has caused the central anterior superior part 16 (the piece below the chin) to move down toward the central anterior inferior part (the piece above the breastbone) 18. The left anterior lateral part 22 and left posterior inferior part 24 have also been caused to contract and rotate relative to one another and the central posterior inferior part 26 and central posterior superior part 28 have moved apart. Following impact, it is possible that the recoil of the head and/or body could be thrown backwards; potentially causing additional injury to the head and spine, especially as the wearer may have lost consciousness or have a reduced muscular response to resist the secondary movement. In practice, such recoil movements may well cause a more harmful injury than that inflicted from the initial impact; or the original injury may be further compounded or exacerbated by the secondary movements. Indeed, in certain applications (such as "American" football) the subsequent swinging of the heavier, helmeted head can prove more injurious to the athlete than the initial inline impact.

Consequently, the present invention attempts to minimize the severity of such injuries, by prohibiting, resisting and/or restricting movement between component parts, and thereby dynamically immobilizing the head and/or neck during the impact, and possible after recoil. Additionally, depending on the circumstances, the immobilized configuration may be held temporarily or until emergency medical care is available; or alternatively, subsequent secondary movements may also be resisted or restricted as the collar dynamically adjusts to a secondary modified immobilization configuration.

The cervical collar brace device 12 is typically intended to be worn as part of the safety equipment associated with high-risk activities undertaken by individuals in sports (e.g. race car drivers and athletes such as football players), entertainment (stunt persons) and military, police or security personnel. In circumstances where a helmet is worn by the wearer of the brace device, one or more of the component parts may be tethered or otherwise connected to the helmet. Moreover, the helmet may itself be formed of one or more parts, at least one of which may itself act as a component part relative to the component parts of the brace device; thereby providing additional stability between the brace device and helmet, and consequently contributing supplemental support between the head and neck. Where the user is seated, all or part of the brace device could be provided on the seat.

Figure 3:
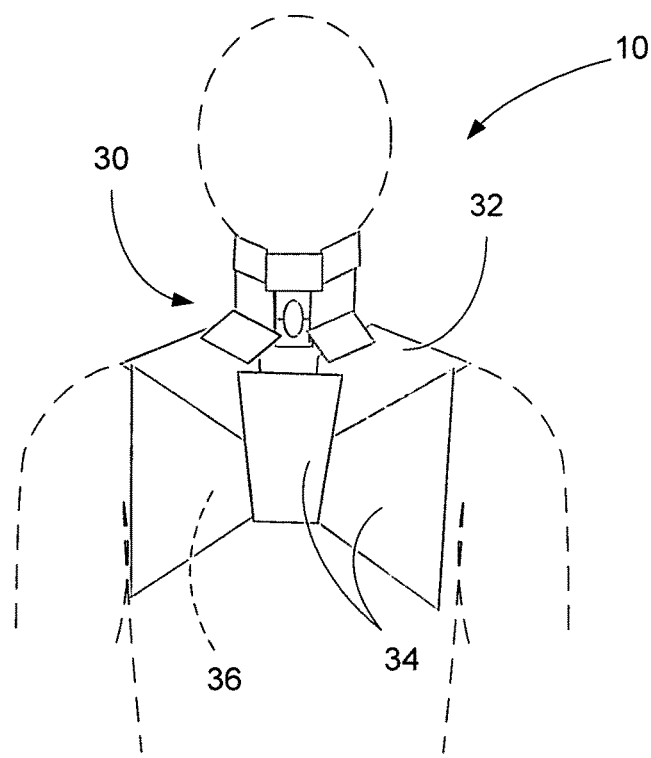
FIG. 3 shows a simplified drawing of an alternate embodiment of the brace device of the present invention, wherein the brace device comprises component parts located around the cervical portion of the spine, with additional support being provided from component parts provided on the shoulders, chest and upper back of the wearer.

FIG. 3 shows an alternate embodiment of the brace device 12 depicted in FIGS. 1 and 2, where the brace device comprises component parts 30 around the cervical portion of the spine, with additional support being provided from component parts provided on the shoulders 32, chest 34 and upper back 36 of the wearer 10.

It should be readily apparent that the responses described above in relation to a frontal impact can equally be appropriately directed to side, rear and combination impacts or other sudden changes in movement.

The brace device of the present invention may comprise internal and/or external movement sensing means for determining any external forces being applied to the wearer 10. This force will manifest itself in two ways: causing the head to be pushed in one direction (angular movement) as well as a downward (translational) movement on the head. Typically the movement sensing means are operated continuously during any activity potentially requiring support from the brace device 12. Movement sensing means include, but are not necessarily limited to, accelerometers, gyroscopes, force-transducers, pressure sensors, strain gauges and the like. Generally the brace devices will utilize accelerometers and gyroscopes; although the device may incorporate any of these or other sensing devices or products.

Gyroscopes can detect variations in the inclination or the brace device, namely pitch and yaw. Accelerometers monitor the magnitude and direction of acceleration (the rate of change in velocity) as a one, two, or three dimensional vector quantity that can detect changes in orientation and the application of shocks. Preferably, the accelerometers utilized are three dimensional (triple-axis) detecting accelerometers, but combinations of these sensors can achieve similar goals. As with presently available airbag deployment mechanisms, accelerometers may be used to detect the rapid negative acceleration (deceleration) of the vehicle and the brace device wearer and thereby determine when a collision has occurred, and provide signals and/or data relating to the severity of the impact.

These movement sensing means may be deployed externally, being mounted on one or more of the component parts, such as on a chest piece, or carried independently by the wearer 10, or be linked to the vehicle or device to which the wearer is active or associated. For example, a wearer in a vehicle may have a brace device 12 that is in communication with the vehicle's airbag sensors and/or the dynamic stability control sensors (controlling vehicle handling in response to cornering and braking forces etc); where the brace device is activated completely or partially upon certain of the vehicle systems experiencing one or more predetermined conditions. The movement sensing means may also be deployed internally within the brace device; for example, on one or more of the component parts. Modern accelerometers, gyroscopes and other sensing devices are often very small micro electro-mechanical systems (as evidenced by their use in many handheld consumer electronic devices), which facilitates such usage.

Typically the accelerometer and/or gyroscopes will provide a three-dimensional vector that can be incorporated in the determination of an appropriate reaction in the partial or complete activation of immobilization of the brace device 12.

The movement sensing means enable the detection of forces that potentially inflict supra-physiological strains on the wearer. Upon receipt of one or more output signals generated and communicated to a microprocessor control means by the movement sensing means, the microprocessor control means analyzes and interprets the received signals and determines, in accordance with preprogrammed parameters and criteria, whether the output signals are indicative of potentially injury inflicting movement or change in movement.

In the event that the microprocessor determines that the movement of one or more component parts of the brace device should be prohibited, restricted or resisted, the microprocessor activates movement resisting means, located on one or more of the component parts. These movement resisting means are operable to prohibit and/or resist movement of the component parts relative to at least one other component part. The movement resisting means may be activated, deactivated or dynamically controlled when the control means determines a movement requires support, or a change in support, of the spine. The movement resisting means are typically electrically activated micro-spot electromagnetic lock assemblies 40, as shown in FIG. 4, comprising a catch-plate 42, having conductive spots (flat spots), and an electromagnetic lock device 44, having double concentric electrical elements (target spot).

The microprocessor may be programmed with specific parameters and criteria that are refined and nuanced for the particular needs of the wearer and/or activity. The typical algorithm for calculation of net force vectors follows the Pythagorean Theorem: if the acceleration in three-dimensions has a value of x for the vertical (up-down) axis, y for the horizontal (left-right) axis, and z for the horizontal (forward-back) axis, then the formula for net acceleration (n) is expressed as $n^2=x^2+y^2+z^2$. The absolute value of a net acceleration that exceeds certain parameters, and/or certain limits on the individual parameters, will trigger the device to immobilize. There may also be individual customized settings for the duration and strength of the immobilization force applied. In general, vertical translation is less well tolerated than lateral movements, so these parameters may typically have lower thresholds for activation.

The type of locking mechanism appropriate for immobilization of the brace devices may vary across different needs and applications. There can, for example, be mechanical immobilization, such as an electrostatically activated form of hook-and-eye fabric (like Velcro™); where in the resting phase the fabric can move smoothly, but upon activation of an appropriate electrical, mechanical, chemical or magnetic signal the fabric is caused to become "sticky". Chemical immobilization through chemical bonds could also be applied as a locking mechanism, or other alternative types of physical locking mechanisms. However, in FIGS. 5a and 5b a simple system for immobilization is described, involving the use of electromagnetic locks.

Figure 4:
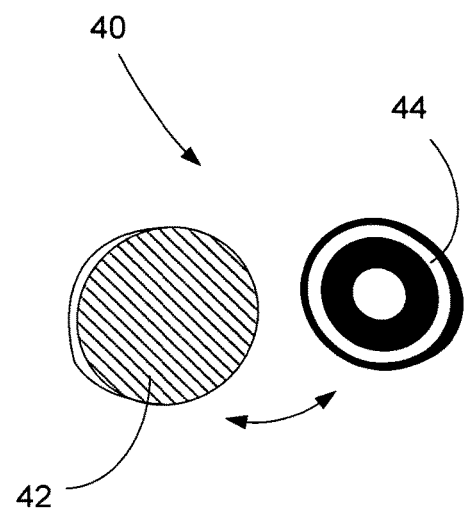
FIG. 4 shows an electromagnetic locking assembly, with corresponding engageable catch-plate and electromagnet components.
Figure 5A:
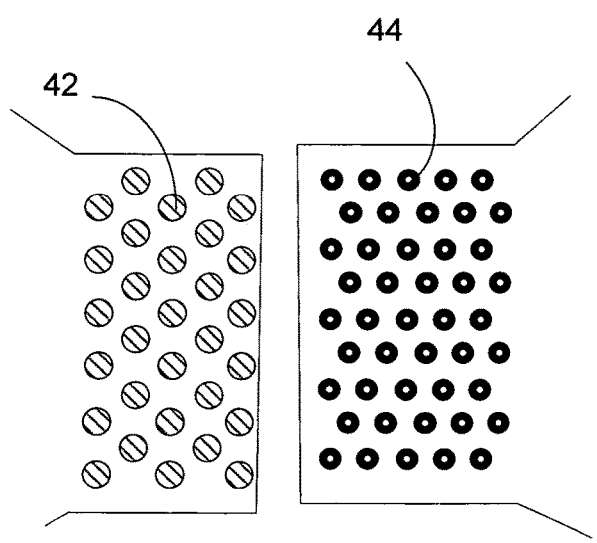
FIGS. 5a and 5b show the electromagnetic locking assemblies of FIG. 4, located on the mating (overlapping) portions of adjacent component parts.

FIG. 5a shows several small electromagnetic lock assemblies 40 of FIG. 4, affixed to partially or completely overlapping portions of the component parts of the brace device 12. One component part comprises an interface area of catch-plates 42 and the other has a complementary area of electromagnetic lock devices 44. The complementary areas are provided in areas that facilitate activation of a locked brace device interface in normal and anticipated abnormal positions.

The two sets are laid out so that the maximum number of productive contacts will be made, and no short-circuits exist. In the preferred embodiment, each interface is charged with a 4 volt, 0.015 amp continuous draw that will divide the equivalent force of 4 lbs force across the active electromagnetic lock assemblies. Consequently, a hexagonal pattern is formed, such that the size of the flat spots are typically 25% larger in diameter than the target spots, the target spots are separated by the diameter of the flat spots, and the flat spots spaced apart at a distance calculated at 110% of the target diameter.

The initial dimension chosen for the target spots is an approximate outer radius of 0.5 mm (outer contact is 0.05 mm thick, insulator is 0.2 mm thick and the inner spot radius is 0.2 mm). This configuration substantially prevents any target spot from coming into contact with more than one flat spot. Each target spot is consequently approximately 1.0 mm in diameter, spaced 2.25 mm apart (center to center).

Each flat spot is approximately 1.25 mm in diameter, spaced approximately 1.1 mm apart.

On a 1 cm overlap that is 3 cm long, this will result in a grid of 3×9 target spots and a grid of 4×11 flat spots. While this may not be a linear matching, the variable spacing allows for there to be a few target spots in direct contact with flat spots at all times, without needing to be realigned first.

Figure 5B:
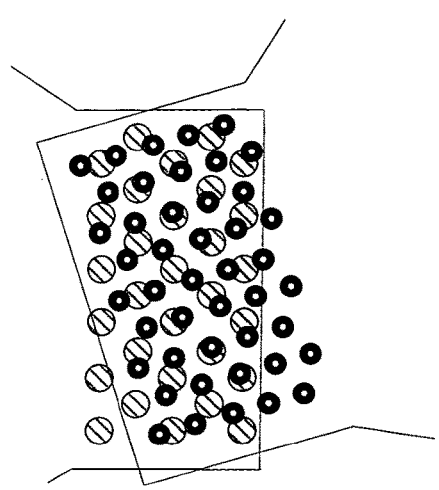

FIG. 5b shows two complementary portions of the component parts of the brace device, rotated and linearly moved in an overlapping configuration that enables immediate immobilization or resisted movement.

A power source, such as a battery located in the chest plate component part, or connected externally to the brace device 12, maintains an electric charge across the electromagnetic lock assemblies 40 while activated. The initial discharge, which needs to be a higher current delivered to maintain a stronger force for immobilization, may be delivered by a capacitor charged by the battery, or there may be a battery that has a high enough discharge rate to achieve this force applied across the multiple electromagnetic locks simultaneously. Once activated, and once the initial time period of maximum immobilization passes (as programmed), the force applied may reduce to a lower force once the collision event has ended.

In a collision event, for example, this charge may be held until emergency services arrive. The brace device may then be deactivated or connected to a supplemental power source. The initial charge applied is typically a higher rating in order to apply maximum holding force to the interfaces holding the component parts. However, the charge may then be lowered to maintain the position after a predetermined time, for example after the first minute has passed since activation. This reduction in supplied charge allows for maximum battery life, while still maintaining sufficient holding force to immobilize spine of the wearer. This prevents movement of the neck or back from the position attained at the time of injury, minimizing the chance of subsequent movement-related injury, but allows emergency medical service personnel (EMS) then to deactivate the brace device, reposition the head if necessary under controlled supervision and re-establish a preferred immobilization position.

Alternatively, in a temporary stress situation, for example a racing driver or pilot being subjected to excess G-forces, the brace device 12 may provide temporary bracing for the duration of the stress inducing situation (cornering, braking etc). In such circumstances, the activation of the brace device, and accompanying provision of applicable charge and holding force to the component parts, is more dynamic and changeable.

Insulated flexible wires attach the individual component parts to each other to carry the electric current, as well as to carry the output signals generated by movement sensors to the microprocessor and the electronic signals to the movement resisting means. The brace device could also incorporate a wireless distress signal generating mechanism, operable to notify emergency crews in the event of the deployment of the device. There are multiple component part interfaces, each of which is separately charged from the battery; consequently, the brace device may also be provided with an alarm mechanism to provide a warning sound to alert the wearer if any contacting interfaces are dysfunctional.

In an alternative embodiment, the catch-plate side of the component part may be provided only with a smooth flat conductive surface, with all target spots contacting this single conductor. In another alternative embodiment, the hexagonal shaped pattern of the flat spots is located with insulated spaces calculated at approximately the thickness of inner spot of the electromagnetic lock, to prevent multiple contacts.

Commercially available electromagnetic lock assembles of the kind described above exhibit a holding force capable of holding approximately 25 lbs (11.3 kg), using operating voltages of 24VDC, 24VAC or 120VAC/60 Hz. This unit will have a continuous current draw of 0.015 Amps, (regardless of whether the current used is direct or alternating, and regardless of the voltage applied). The resistance to shear forces of this assembly is such that it requires a much greater orthogonal force to displace a force applied.

In the preferred embodiment, the component parts would be manufactured as individual plates, having edges with slide guards that prevent them from sliding too far in any one direction, while maintaining the electromagnetic lock assemblies in generally layered apposition. The plates are preferably formed from injected molded plastic, but polycarbonate, Kevlar™, nano-machined substances, metals and other woven or machined materials can be substituted based on the needs and application of the device (military applications may be coated or made with Kevlar to resist bullets, shrapnel, or knife wounds) in order to provide some flexing, and thereby further reducing applied forces in the event of severe physical stresses.

In addition, there would be sufficient overlap between the interfacing plates to allow for a full range of motion, when not activated, in all cardinal ranges of motion (flexion, extension, left and right lateral bending, and left and right rotation), while still having a sufficient number of micro-spots in potential contact to apply an adequate force capable of preventing sliding. As the force required to prevent sliding of the plates would be a substantially orthogonally applied shear to the electromagnetic force, a small electromagnetic force is sufficient to prevent all but the most severe of physical forces from deforming the brace device 12 once activated.

The component part plates' movement is preferably limited so that the edges are not able to slide to the extent that the micro-spots cease to be in contact with each other. This will typically be achieved by having small angled "stops" that prevent too much overlap, and by providing a nylon safety strap on each overlap to prevent complete separation.

Figure 6:
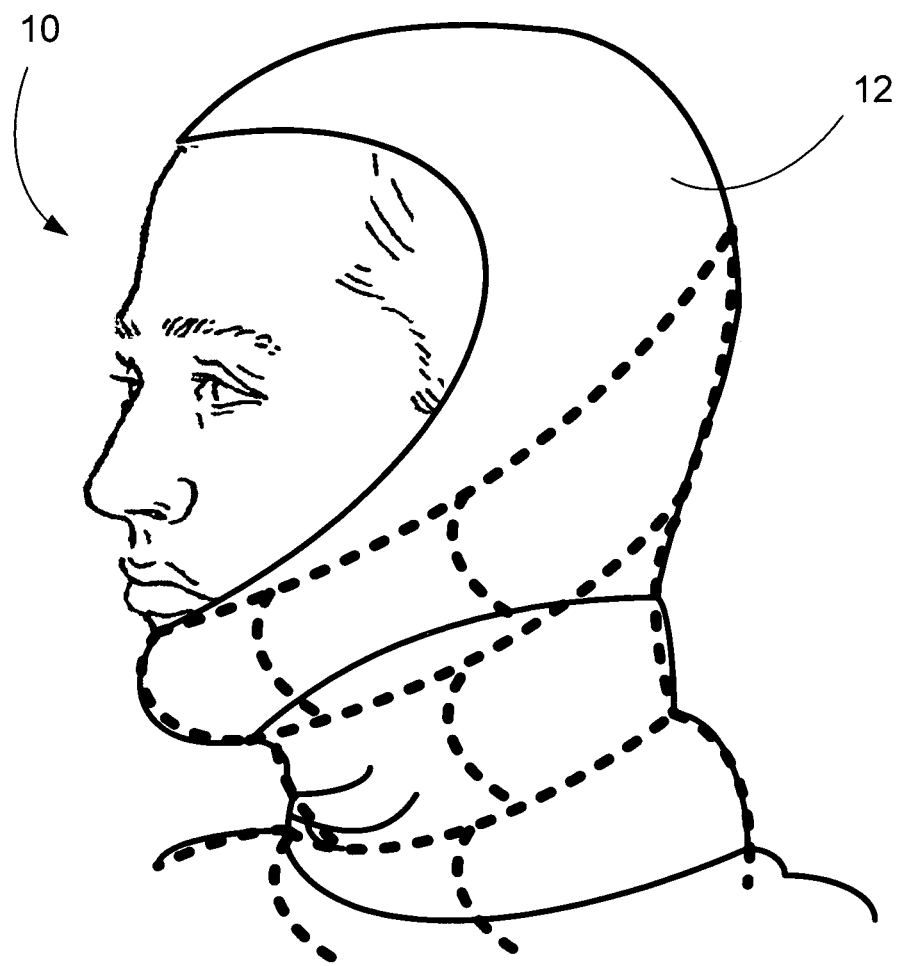
FIG. 6 shows a simplified drawing of an alternative embodiment of the invention adapted to be worn as a balaclava in high-risk activities.

FIG. 6 shows an alternative embodiment of the brace device 12, where the brace device would pull on over the head of a wearer 10 (much like a turtleneck and balaclava, with no sleeves) with component part plates extending down into the chest and back area. The collar would extend up over the lower jaw and behind the inion (bony prominence of occipital bone at the back of the skull just above the neck) to provide full immobilization.

A third embodiment of the invention utilizes "smart materials" or "intelligent textiles" in the brace device. Although, such fabrics are sometimes distinguished in the art (the former sensing environmental conditions or stimuli, and the latter considered capable of also reacting to the conditions or stimuli), no such distinction is made in this specification. The term "smart fabric" is herein used to encompass both possibilities generally. Smart fabrics typically utilize nanotechnology and are generally soft and flexible in normal circumstances, but are able to harden almost instantaneously when subjected to an impact or other external stimulus.

An example of an innovative early electro-conductive smart fabric is ElekTex, developed by Eleksen Ltd, a British company. This product uses technology that sandwiches an electrically conductive, proprietary, knitted textile between carbon-impregnated knitted nylon layers, which in turn are covered with an outer layer similar to woven nylon. The resulting product is flexible and "touch sensitive;" being capable of sensing the position of a touch on the surface, as well as differentiating the intensity of the pressure applied. Another example is the Dow Corning Active Protection System; which is soft, flexible and breathable in normal conditions, but hardens almost instantly upon receiving an impact (and then returns to the flexible state when the impacting force is removed). The Scandinavian Research organization SINTEF has also developed a generally soft and flexible material called "d3o", which uses intelligent molecules that flow freely until subjected to pressure, whereupon they instantly lock to harden and absorb/distribute the impacting force. This product is known to be used in helmet lining.

It will be appreciated from the above, that hardening of the smart material in response to a direct impact is known. However, hardening of the smart material (without the material necessarily being subjected to a simultaneous direct impact) in response to a movement or a change in movement determined to be potentially injurious is not contemplated in the art. The present invention envisages use of garments or other suitable products utilizing smart fabrics that form the brace device, or form part of a brace device. The material could be activated by application of an appropriate stimulus, such as a current, a change in current, or the stopping of the current; such that the smart fabric is caused to "freeze" in its current state, position or shape, or which demonstrates variable rigidity to provide resistance to movement. The tensile properties within one or more regions of the fabric being altered in response to the stimulus, which activates, deactivates or dynamically controls fabric hardening means; thereby partially or substantially hardening these regions. The stimulus and/or hardening means may be thermal, chemical, mechanical, electrical, magnetic or from another appropriate source. For example, the above mentioned products could readily be caused to harden by mimicking, in response to the movement or change in movement, the stimulus and reaction resulting from a directly impacting event.

The present invention also contemplates movement sensing means being provided on one or more locations on the smart fabric and/or other elements of the brace device (if applicable). The smart fabric may additionally include other sensors. For example, researchers have found that molecules of a material that reacts with human serum albumin can be added (coated on) to the fibers of the fabric; which molecules detect the presence, location and intensity of bleeding (on application of an electric current through the fibers and measuring the changing conductivity across the fabric). Other sensors may also be included on the brace device, being a capable of monitoring the physical condition or heath of the wearer, including the heart rate, body temperature and blood pressure etc. All of this information may be communicated directly or wirelessly to emergency personnel that respond to an injury inflicted on the brace device wearer in order to assist them in the appropriate care and treatment.

It will be appreciated that the embodiments described in this specification relate to the support of the spine of a wearer in response to conditions that potentially inflict physiological stresses and strains. This invention contemplates that appropriate modifications to the brace device could readily be made to control or prevent unwanted or abnormal movement in other areas of the body, such as hinged joints, for use in medical rehabilitation, training, or other situations where the potential for injury is high.

Figure 7:
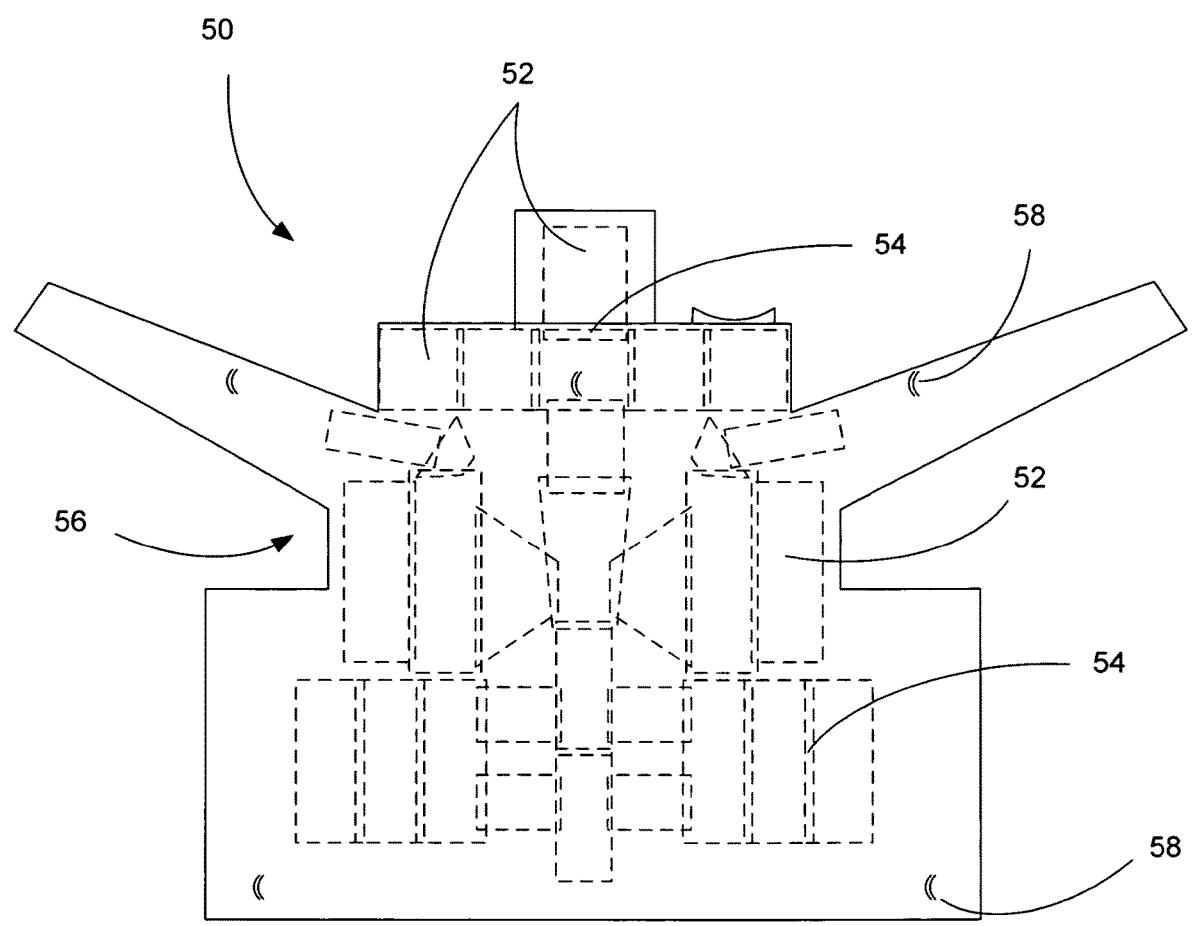
FIG. 7 shows a very simplified conceptual drawing of the flexible extrication system device (plate shapes, sizes and configurations are not indicative of actual relative dimensions)

FIG. 7 shows an alternative embodiment of a somewhat simplified (more static) variation of the dynamic support systems described above which is primarily used for the extrication of patients after accidents. The current standard methodology for extrication of a patient of a motor vehicle accident involves placement of a disposable rigid cervical collar (such as the Stifneck™ device; by Laerdal, Wappingers Falls, N.Y.) followed by placement of the KED by EMS personnel. Demonstration videos show this process taking approximately 5 minutes, when applied in a training situation where the "patient" is sitting in a chair; not in a vehicle with various impediments to a safe and expedient extrication.

Currently, the KED systems available in the market is heavy (8 pounds), cumbersome, and difficult to place on patients without moving them. The major stabilizing agent of the KED is the backboard, which needs to be passed in its full thickness (1 inch) behind the patient's torso. The device takes up valuable space in any EMS-type vehicle (for example, 34 inches by 11 inches by 6 inches), and once in place makes it difficult to evaluate the body of the patient in any of the areas being secured without risk of additional injury.

FIG. 7 shows a flexible extrication system 50 is comprised of multiple substantially rigid plates 52 that are each appropriately shaped and contoured to suit the generalized body habitus (at the area of the body where it will be applied) of the average patient. Many of the plates are moveable relative to other plates and have regions of partial overlap 54 with one or more other plates with which they can be engaged and locked using appropriate movement resisting means and mechanisms described in previous embodiments above.

All plates are connected to a waterproofed central power/control device via flexible wire cables. The plates of the flexible extrication system are affixed to a Lycra™-like lining (inside and out) and this liner shell 56 will maintain general shape and alignment yet prevent over-distraction. A second reusable liner, made of a water-resistant fabric similar to a Nylon/Lycra mesh, preferably envelopes the device and is provided with several loops 58. The flexible extrication system device can be stored flat, but more typically will be stored wrapped up in a roll to save space, with the second liner already attached (the roll diameter is approximately 6 inches when stored). On the outside of the roll (in sleeves) will be located two substantially rigid, but slightly flexible, plastic pull-rods 60 (shown in FIG. 8), being approximately 5 mm in diameter. These pull-rods may be attached on the outside of the device, and have one or more engaging means, in the form of tabs 62 provided on the ends, which tabs are operable to engage with the loops on either side of the flexible extrication system device. The loops are preferably provided at the shoulder straps 64 and the chest straps 66, but additional tabs could be provided on the pull-rods that correspond with other loops on the device or which enable pull and pulling. In this manner, the device can be used from either the driver's or passenger's side of the vehicle.

Figure 8A:
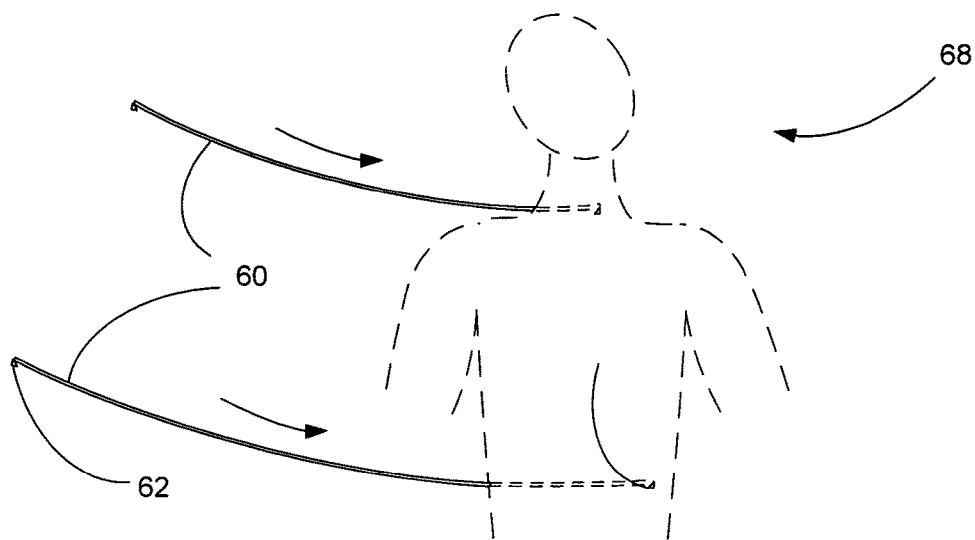
FIGS. 8(a) to 8(d) show the manner in which the flexible extrication system device may be applied to a trauma patient in readiness for extrication; with (a) showing pull-rods positioned behind the neck and back to facilitate positioning of the proposed flexible extrication system device; (b) and (c) showing the flexible extrication system device being positioned; and (d) showing the patient with the flexible extrication system in place after activation.
Figure 8B:
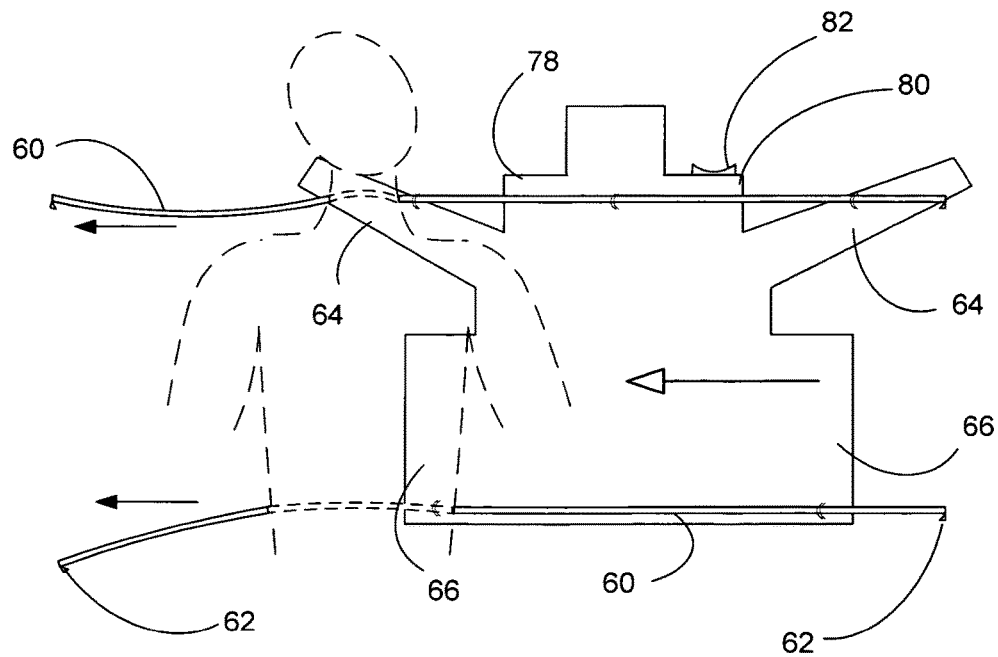
Figure 8C:
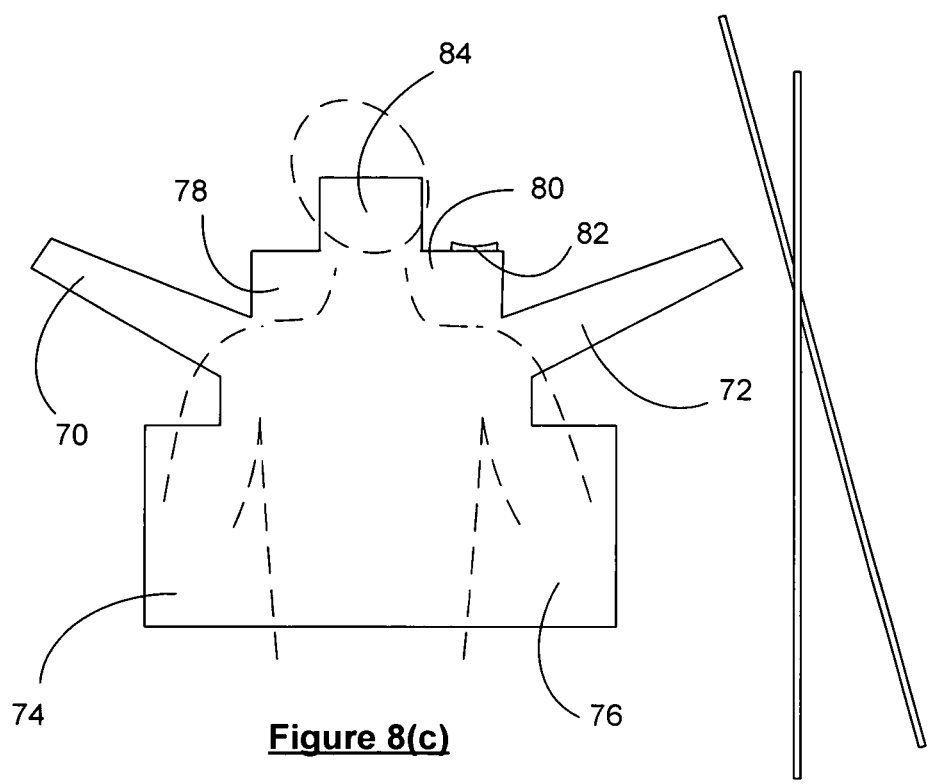
Figure 8D:
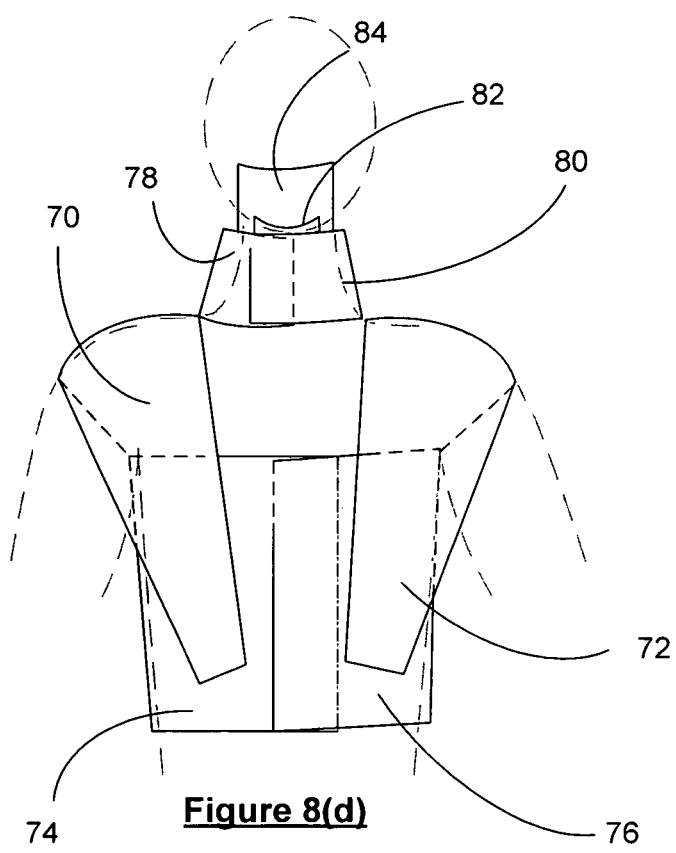

The small diameter pull-rods 60 are independently passed behind the body of the person 68 to be extricated; one substantially around the small of the back and the second substantially behind the neck, as shown in FIG. 8(a). The pull-rod tabs 62 are engaged in the loops of the straps and the pull-rods are then be used to pull (or push) the now unrolled device behind the patient; the rods are then disengaged and removed (shown in FIG. 8(c)). The individual straps 70, 72, 74 and 76 are passed in front of the patient, thereby pulling both sides of the flexible extrication system around to overlap in front of the patient, and the chest and shoulder straps then secured tightly in front of the patient using Velcro (or other appropriate fastening mechanism). The chin straps 78 and 80 will be fitted snugly under the chin, with the chin located in the chin portion 82. FIG. 8(d) shows the flexible extrication system device secured around the patient 68. It will be appreciated that the device directly incorporates head and neck immobilization, including direct support for the skull (84), without need for a separate cervical collar.

The individual shaped plates 54 of the flexible extrication system device 50 contour to the patient's body and the degree of interfacing overlap between each plate can be varied; so the device will only need minimal adjustments to get it ready for activation and immobilization based on the patient's size. The adjustable nature of the device accommodates to secure morbidly obese patients, pregnant patients, and children; providing immobilization from the region of the lumbar spine to the head, inclusive of lumbar, thoracic and cervical regions of the spine. In addition, the ability to contour to the patient will allow for patients of atypical body habitus (having scoliosis or kyphosis, for example) to be equally stabilized.

Once the device is secured (as shown in. FIG. 8(d)), the flexible extrication system is activated, and the electromagnetic locks located at the regions of overlap 54 tighten and freeze the plates 52 into place. The contoured shapes of the moveable plates cause an appropriate compressive, supportive force to be applied to the patient. In a more sophisticated variant of the flexible extrication system, the magnetic locks can be caused to provide a measure of pre-tensioning prior to locking. The patient is then removed from the vehicle as a single block, using the attached handles (not shown) to pull at the hips and shoulders so as not to move the neck. The electromagnetic locks hold the plates in place, preventing relative movement of one body part to another, which reduces the chances of worsening of neurological or medical conditions.

The patient is then strapped, if necessary, onto any commercially available spine board (as if not wearing a KED (Kendrick Extrication Device) or the flexible extrication system). The straps already attached to the board will readily stretch around the flexible extrication system on the patient, which will hold the patient and flexible extrication system on the board for transportation onto the stretcher and from there into the EMS (emergency medical services) vehicle and out on arrival at the ER (Emergency Room). Once in the ER, the patient can be safely removed from the spine board as the flexible extrication system will hold the person stably and any further long-board immobilization is unnecessary. The system will also have the capability to have one side 74 and/or 78 or the other side 76 and/or 80 turned off and unstrapped, in order to permit log-rolling of the patient and examination of their back, neck and sides, one side or portion at a time, while maintaining the immobilization on the other (dependent) side or portion. With a single press of a button the first side (or a portion thereof) could be reactivated, and then a second press of a button causes the other side to be deactivated. Safety protocols will be present to prevent accidental deactivation during transport.

The device will likely have some minimal radiographic signature upon imaging, but given the current technology in flexible circuitry, this will have minimal impact (wires are small, while the majority of the device will be radiolucent) upon imaging of body anatomy; and because of the tight fit to the individual patient it will be easier to fit into CT scanners than the KED.

Finally, when the flexible extrication system is no longer needed to support/immobilize the patient, the device will be deactivated fully and removed. If the patient still needs cervical immobilization, due to a fracture or other instability, a cervical collar can be placed by the ER or neurosurgical team (which is often done anyway since the typical extrication cervical collar is usually replaced due to its abrasive edges). At that time, the flexible extrication system liner can be removed for later cleaning and decontamination back at the station, and the main part of the device and liner shell 56 can be cleaned and if necessary decontaminated by EMS. A fresh liner is reapplied and the device is rolled up again, with the plastic rods reattached to the outside for storage on the EMS vehicle ready for repeat deployment.

It is believed that the flexible extrication system will improve upon the current standard of care provided by emergency medical services (EMS) and First Responders in immobilizing the spine of individuals with injuries to the head, neck or spine and facilitating treatment. The flexible extrication system enables effective securement and immobilization of the full spinal area of a human of any age and/or body type, thereby reducing the potential of further injury during in-field stabilization and subsequent transport by EMS providers whether being transported on a spine board or not.

Is will be appreciated that the flexible extrication system consists of a combination of carefully shaped, moveable overlapping and interlocking plates, defining a flexible brace that can be easily configured to the patient's body. When electromagnetically activated (and locked) the plates in combination form a rigid brace for the provision of immobilization and support to the lumbar and thoracic back, neck, and head of a person involved in an accident, such as a motor vehicle accident, who may be at risk for or is already suffering from a spinal injury. In comparison with other available devices that require pre-configuration and pre-adjustment prior to fitment, the flexible extrication is essentially self-fitting; with the adjustment being automatic and occurring after fitment.

The plates are generally contoured for accommodation of certain areas of the body and certain plates are moveable relative to one or more other plates, in rotational, shear and/or linear orientations, and the combination of the pieces may be extended or contracted within defined parameters. Together, the numerous plates of the flexible extrication system allow relatively flexible movement while being positioned around the head, neck and/or back of the patient (for example, while still in the vehicle), but upon activation the plates will be drawn together to an appropriate supportive force (taking up the slack and "molding" to the shape of the patient). Although the contoured nature of the plates largely achieves this, the device could additionally be either pre-programmed or calibrated by the First Responder to provide appropriate rigid immobilization and support (accounting for extrication difficulties or specific injuries). The number, shape and size of the plate parts may be varied to accommodate differences in the size, shpe and purpose of the brace device. Additionally, depending on the circumstances, the initial immobilized configuration may be held temporarily (perhaps to extricate the patient from the vehicle) and then deactivated and easily readjusted by emergency personnel to a more appropriate secondary modified immobilization configuration.

When the flexible extrication system detects activation by First Responders, a microprocessor triggers electrically activated micro-spot electromagnetic lock assemblies located on one or more plates; prohibiting movement of the plates relative to at least one other plate. These locking mechanisms comprise catch-plates (conductive flat spots) located on one plate and partially or completely overlapping corresponding electromagnetic locks with double concentric electrical (target spot) elements located on the other plate. The engagement areas are provided in places that facilitate activation of a locked brace device interface in anticipated support configurations. Generally, the electromagnetic type of locking mechanism is appropriate, although other movement resistant mechanisms for the immobilization of the brace devices may be applicable for different needs and applications (such as disposable devices); potentially including mechanical immobilization, where in the resting phase the plates remain flexible relative to one another, but upon activation of an appropriate electrical, mechanical, chemical or magnetic signal the locking interface is caused to become "sticky".

Upon activation, each locking interface is charged with a continuous electrical draw (typically 0.015 Amps) that will spread the resistive force across the active electromagnetic lock assemblies. A power source is provided by a battery located in the flexible extrication system or connected externally to ensure electric charge across the electromagnetic lock assemblies while activated. Insulated flexible conductors will connect the individual component parts to each other to carry the electric current. Commercially available electromagnetic lock assembles of the kind described above exhibit a holding force capable of holding approximately 25 lbs (11.3 kg) using operating voltages of 24VDC. The resistance to shear forces of this assembly is such that it requires a much greater orthogonal force to displace a force applied.

The flexible extrication system utilizes battery power with an integrated and waterproofed source that is rechargeable using lithium-ion type batteries (the batteries will typically be charged from the 12VDC power supply of the EMS vehicle). Once the patient is extricated and placed in the EMS vehicle, the device could again draw power from the EMS vehicle and then revert again to battery supply upon arrival in the ER (where the device could be either under battery or external power supply).

For transportation and for radiology procedures, a battery supply of at least one hour is appropriate, with a warning when battery life is waning. The electrical properties necessary to maintain the holding forces with the electromagnetic locks will determine the materials to be used in the device, but special care will be taken to ensure that the systems are adequately insulated and grounded for maximum safety for both safety personnel and the patient being extricated (even when under water). A built-in capacity to sense whether any locking points are failing to maintain adequate hold or tension may be provided, and some feedback (such as LEDs on the front of the device) will inform the EMS personnel where the failures are to facilitate optimal immobilization. Finally, when the battery life is near its end, a separate LED could indicate required replacement. The maintenance of the device will consist primarily of changing the battery when an LED warning light shows that the battery is no longer holding an adequate charge; there will be no other user-serviceable parts.

The plates will preferably be formed from injected molded plastic, and relative movement between plates will be limited so that the edges are not able to slide to the extent that the micro-spots cease to be in contact with each other. This will typically be achieved by having small angled "stops" that prevent excessive overlap.

A more advanced version of the flexible extrication system may utilize "smart materials" or "intelligent textiles" in the brace device, which typically utilize nanotechnology and are generally soft and flexible in normal circumstances, but are able to harden almost instantaneously when subjected to an external stimulus.

The flexible extrication system has ready applicability in protecting the patient from worsening their condition by stabilizing the head, neck, chest, and lumbar spine, and is designed to be used in First Responder applications in lieu of cervical collars or other spinal bracing traditionally used for trauma patients after an accident or injury (such as the Kendrick Extrication Device). Once the patient is supported and removed from the vehicle, the person can be strapped to a spine board; but because the flexible extrication system is both rigid and contoured to the patient there is a much reduced possibility for pressure ulcers to develop in transit. The spine board is typically only necessary as an easy transport media or for those patients having leg or arm injuries that would preclude any movement of the limbs; otherwise for an isolated trunk or head/neck injury the flexible extrication system could itself serve as the spine board.

This device is to be substantially radiolucent (permitting X-rays to pass through), reusable, more compact than the KED, easily cleaned and decontaminated, durable, and will require little additional training for use and general maintenance. The device, as moldable to individual body types, should replace the use of both cervical collars and the KED device, thereby also reducing the need for as many carry collars on an EMS vehicle. There will be a fluid and blood resistant liner that will protect the device and the EMS personnel, which may be disposable or reusable and easily cleaned and decontaminated.

The problematic issues confronted through the use of backboards and KEDS are in many instances avoided, as the flexible extrication system should in most circumstances provide sufficient support independently, replacing the backboard/KED completely. The flexible extrication system:
is easy to use and rapidly deployable, facilitating initial positioning in difficult environments with patients that may be in highly abnormal spinal positions, providing highly simplified fastening/molding of the device around the portion of the spine requiring support (with the click of a button), enabling extrication of the patient while maintaining immobilizing support and prohibiting any substantial subsequent movement; enabling ready readjustment and reactivation of the device when the patient can safely be moved into a more comfortable or appropriate position;

is form fitting; the combination of multiple moveable, shaped plates affords significant flexibility and "moldabilty" to a wide range of body shapes and sizes, as well as abnormal body postures, while also providing a high degree of immobilizing strength and support to all spinal areas;

is durable; not being susceptible to puncture (as with some inflatable devices); and highly durable;

is easily to clean and decontaminate, being made primarily of plastic plates and cloth, with any electrical component parts being sealed and waterproofed;

is compatible with existing equipment, and indeed removing the need for certain equipment in certain applications;

is absorbent, through use of appropriate cloth coverings;

is of variable size, with reduced need for as many sizes due to the in-built adaptability of the plate configurations;

is radio-translucent, substantially facilitating use of X-rays through careful positioning of the radio-opaque components in less relevant areas and the ability to activate/deactivate certain portions of the device and afford partial access to the potentially injured region;

reduces threat of further injury; using flexible rods, the flexible extrication system can be passed behind the patient requiring only minimal repositioning to pull the device behind the body at the small of the back and behind the neck, enabling application while the patient is still in a vehicle; EMS or Emergency Room doctors can log-roll the patient for examination while maintaining immobility; and the patient is less susceptible to pressure sores from over-tightening of chest straps on the existing KEDs, as the flexible extrication system will have a superior fit provided due to the moldable material;

is easily transported and stored; being smaller than the current KED, allowing multiple devices to be carried on a typical EMS vehicle (ambulance, helicopter, boat), weighs less and will be easier to apply, and requires considerably less manipulation of the patient prior to immobilization being achieved (and can be easily readjusted when appropriate to do so);

will replace the need for both cervical collars and KED at the scene of the accident;

will save time, because it will be easier to apply, and application will be partially automated; which will mean having the patient out of the vehicle and ready for transfer to the next level of care sooner.

Because of the superior fit, the flexible extrication system will provide a superior immobilization without causing respiratory restriction due to over-tightening of the chest straps on existing devices. Superior fit will also mean a reduced profile of the device, which will allow for easier use in a CT scanner by emergency room (ER) personnel. Moreover, the device will have the capability of being partially and reversibly deactivated on one side or the other, facilitating examination and evaluation of half of the body during a log-roll examination, while simultaneously maintaining immobilization of the other side. It is believed this capability does not exist in any other device currently on the market and would represent a significant step forward in mitigating one of the major risks of other devices, namely allowing additional injury to the patient during the typical log-roll examination when the different parts of the patient may move relative to one-another if not so constrained.

The vast majority of the cross-sectional area of the flexible extrication system device will be radiolucent. Reusable liners will be easy to wash, change and allow the protection of the First Responders from blood. The flexible extrication system can be deactivated and ready for use immediately after cleaning the main shell and insertion of a fresh liner (it is anticipated that multiple liners will be provided with each device to make sure that there are adequate available between laundering). Finally, physiological sensors can be built into more advanced versions of the flexible extrication system device, saving time for application of similar devices, such as heart monitors, blood pressure monitors, temperature monitors, among others. This information may be transmitted in advance to the ER in anticipation of hand-over from the First Responders.

The plates will be made of a material that is relatively rigid, but radiolucent (plastic, carbon fiber and low density alloys like magnesium are applicable). Different materials may be selected for different parts or for different places on the device, based on the weight of the device and the radiographic impact. For example, maximum radiographic importance is typically focused on the middle of the device in anterior and lateral projections, and some plates may be larger and bear more load than others. Only two locations of the flexible extrication system are likely to have a radio-opaque metal; namely the battery case and microprocessor unit (which will likely be positioned behind and above the head) and the edges of the plates (where the metallic electromagnetic locks will be located). The size and number of magnetic locks will be kept as small as possible and, where possible, the locks will not be in line with the center of the device in order to minimize any overlap with the spinal anatomy. In this regard, consideration is given to optimal positioning of metallic components to ensure minimal impact upon the typical work undertaken in an emergency room situation. Where a relatively small profile and/or high effective holding force is required, due to plate movement configurations or to avoid interference in scanning procedures, it is possible to apply a combination of electromagnetic locks with friction surfaces (etching) that supplement the locking mechanism in a way that once the lock is engaged, little power will be required to maintain the holding force.

Reference is made in this specification to the application of microprocessors that may be used in accordance with the present invention and as applied in some example embodiments. It should be appreciated that the microprocessors may operate as a standalone device or may be connected (e.g., networked) to other microprocessors, computers or devices. In a networked deployment, the microprocessors may operate in the capacity of a server or a client machine in a server-client network environment, or as a peer machine in a peer-to-peer (or distributed) network environment. The microprocessor may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify, actions to be taken by that machine. Further, while a single microprocessor may be described, a single microprocessor shall also be taken to include any collection of microprocessors that individually or jointly execute a set (or multiple sets) of instructions to perform any one or more of the functions described in this specification.

Machine-readable media may be provided, on which is stored one or more sets of instructions (e.g., software, firmware, or a combination thereof) embodying any one or more of the functions described in this specification. The instructions may also reside, completely or at least partially, within the main memory, the static memory, and/or within the processor during execution thereof by the computer system. The instructions may further be transmitted or received over a network via the network interface device.

In example embodiments, a microprocessor may be configured to perform certain operations. In other embodiments, the device may include dedicated circuitry or logic that is permanently configured (e.g., within a special-purpose processor) to perform certain operations. It may also comprise programmable logic or circuitry (e.g., as encompassed within a general-purpose processor or other programmable processor) that is temporarily configured by software to perform certain operations. It will be appreciated that the decision to implement the device mechanically, in the dedicated and permanently configured circuitry, or in temporarily configured circuitry (e.g. configured by software) may be driven by cost and time considerations. Accordingly, the term "microprocessor" should be understood to encompass a tangible entity, be that an entity that is physically constructed, permanently configured (e.g., hardwired) or temporarily configured (e.g., programmed) to operate in a certain manner and/or to perform certain operations described herein.

The invention claimed is:

1. A brace device for the support of a wearer, the brace device comprising:
   a flexible smart fabric defining a shape to partially or substantially enclose or lie adjacent to one or more portions of the thoracic, lumbar and cervical portions of the spine of the wearer; and
   a fabric hardener integrated with at least a portion of the flexible smart fabric, the fabric hardener configured to reversibly bias the portion of the flexible smart fabric between a flexible configuration and a hardened configuration,
   a sensor in communication with the fabric hardener and configured to transmit a signal to the fabric hardener thereby biasing the fabric hardener between the flexible configuration and the hardened configuration at the time of an injury;
   wherein in the flexible configuration, the portion of the flexible smart fabric is in a partially or substantially flexible configuration, facilitating positioning, fitment or adjustment of the device around the wearer;
   wherein in the hardened configuration, the portion of the flexible smart fabric is fixed in a position or shape of the portion of fabric at the time the biasing signal is transmitted corresponding to a position or shape of the one or more portions of the spine of the wearer at the time of the injury thereby to prohibit, restrict and/or resist movement of the one or more portions of the spine of the wearer.

2. The brace device according to claim 1, wherein the sensor transmits signal upon sensing a thermal, chemical, mechanical, electrical, and/or magnetic activating stimulus.

3. The brace device of claim 2, wherein the brace device further comprises sensors for monitoring the physical condition or the wearer.

4. The brace device according to claim 3, wherein the brace device further comprises sensors for monitoring the physical condition or the wearer and wherein the sensors monitor the heart rate, body temperature, blood pressure and/or the presence and/or location of bleeding.

5. The brace device of claim 1, wherein one or more predetermined regions are configured to be selectively activated or deactivated.

6. The brace device of claim 1, wherein the signal is indicative of a force exerted on the smart fabric and the fabric hardener is configured to be biased in proportion to said force exerted on the smart fabric.

7. A brace device for the support of a wearer, the brace device comprising:
   a flexible smart fabric, operable to partially or substantially enclose and/or lie adjacent to one or more portions of the thoracic, lumbar and/or cervical portions of the spine of the wearer; and
   a fabric hardener, operable to partially or substantially harden one or more regions of the smart fabric selectively upon application of at least one activating stimulus at the time of an injury, thereby to prohibit, restrict and/or resist movement of one or more portions of the spine of the wearer, and the one or more regions of the smart fabric are operable to be selectively deactivated, returning the one or more regions of the smart fabric to a partially or substantially flexible state, upon variation of the at least one activating stimulus;
   wherein one or more predetermined regions of the smart fabric are in a partially or substantially flexible configuration when the fabric hardener is not activated or is deactivated, facilitating positioning, fitment and/or adjustment of the device around the wearer, and upon activation of the fabric hardener is operable to cause the one or more predetermined regions to assume a substantially rigid configuration corresponding to a position or shape of the one or more portions of the spine of the wearer at the time of the injury and thereby partially or substantially support and/or immobilize of at least a portion of the spine of the wearer; and
   wherein in the substantially rigid configuration, the one or more predetermined regions are fixed in shape and position of the region upon variation of the activating stimulus.

8. A brace device for the support of a wearer, the brace device comprising:
   a flexible smart fabric, defining a shape, consisting of several moveable and over lapping component parts, to partially or substantially enclose or lie adjacent to one or more portions of the thoracic, lumbar, cervical portions of the spine, shoulders, chest, and chin of the wearer;
   wherein the component parts are affixed to one another or lie on the wearer;
   a fabric hardener integrated with at least a portion of the flexible smart fabric, the fabric hardener configured to reversibly bias the portion of the flexible smart fabric between a flexible configuration and a hardened configuration;
   wherein the fabric hardener is immediately biasable from the flexible configuration to the hardened configuration;
   a sensor in communication with the fabric hardener and configured to transmit a signal to the fabric hardener thereby biasing the fabric hardener between the flexible configuration and the hardened configuration at the time of an injury;

wherein in the flexible configuration, the portion of the flexible smart fabric is in a partially or substantially flexible configuration, facilitating positioning, fitment or adjustment of the device around the wearer;

wherein in the hardened configuration, the portion of the flexible smart fabric is fixed in a position of shape of the portion of fabric at the time the biasing signal is transmitted corresponding to a position or shape of the one or more regions portions of the spine of the wearer at the time of the injury thereby to prohibit, restrict and/or resist movement of the one or more portions of the spine of the wearer.

9. The brace device according to claim 8, wherein the sensor transmits a signal upon sensing a thermal, chemical, mechanical, electrical and/or magnetic activating stimulus.

10. The brace device of claim 9, wherein the brace device further comprises sensors for monitoring the physical condition or the wearer.

11. The brace device according to claim 10, wherein the brace device further comprises sensors for monitoring the physical condition or the wearer and wherein the sensors monitor the heart rate, body temperature, blood pressure and/or the presence and/or location of bleeding.

12. The brace device of claim 8, wherein one or more predetermined regions are configured to be selectively activated or deactivated.

13. The brace device of claim 8, wherein the component parts consist of at least a central anterior superior part, a central anterior inferior part, a central anterior middle part, a left anterior lateral, a right anterior lateral part, a left posterior inferior, a right posterior inferior part, a central posterior inferior part, or a central posterior superior part.

14. The brace device of claim 13, wherein less, but not less than one, component parts exist in an embodiment.

15. The brace device of claim 13, wherein electromagnetic lock assemblies secure mating portions of adjacent component parts.

16. The brace device of claim 8, wherein substantially rigid plates are integrated between component parts of the smart fabric.

17. The brace device of claim 16, wherein the substantially rigid plates are movable relative to other plates and have regions of partial overlap.

* * * * *